United States Patent [19]
Lovey et al.

[11] Patent Number: 4,737,508
[45] Date of Patent: Apr. 12, 1988

[54] 1-ARYL-1-(1H-AZOL-1-YLALKYL)-1,3-DIHYDROISOBENZOFURANS, RELATED DERIVATIVES AND PHARMACEUTICAL COMPOSITIONS THEREOF USEFUL AS ANTIFUNGALS

[75] Inventors: Raymond G. Lovey, West Caldwell, N.J.; Arthur J. Elliott, Sloatsburg, N.Y.

[73] Assignee: Schering Corporation, Kenilworth, N.J.

[21] Appl. No.: 697,539

[22] Filed: Feb. 1, 1985

[51] Int. Cl.$^4$ ................ C07D 405/06; A61N 43/653; A61N 43/50
[52] U.S. Cl. ................................ 514/383; 548/262; 548/336; 544/132; 544/139; 544/79; 544/121; 544/130; 544/357; 544/360; 544/366; 544/270; 546/210; 546/189; 514/234; 514/255; 514/324; 514/385; 514/316
[58] Field of Search ................ 548/262, 336; 544/132, 544/139, 366, 370, 79, 121, 130, 357, 360; 546/210, 189; 514/234, 255, 324, 320, 383, 385, 316

[56] References Cited
FOREIGN PATENT DOCUMENTS
A29412  1/1985  Australia ............................ 548/336
2143523 2/1985  United Kingdom ................ 548/262

Primary Examiner—Robert T. Bond
Attorney, Agent, or Firm—Thomas D. Hoffman; Gerald S. Rosen

[57] ABSTRACT

Novel compounds including 1-aryl-1-(1H-imidazol-1-ylmethyl)-1,3-dihydroisobenzofurans such as 1-(4-chlorophenyl)-1-(1H-imidazol-1-ylmethyl)-1,3-dihydroisobenzofuran, and 1-aryl-1-(1H-1,2,4-trizazol-1-ylmethyl)-1,3-dihydroisobenzofurans are disclosed. The corresponding benzo[c]thiopenes, isochromans, and isothiochromans and antifungal pharmaceutical compositions containing same, and methods of using said pharmaceutical compositions to elicit an antifungal response in warm blooded animals having a susceptible antifungal infection are also disclosed.

18 Claims, No Drawings

1-ARYL-1-(1H-AZOL-1-YLALKYL)-1,3-DIHYDROISOBENZOFURANS, RELATED DERIVATIVES AND PHARMACEUTICAL COMPOSITIONS THEREOF USEFUL AS ANTIFUNGALS

BACKGROUND

Field of Invention

This invention relates to the novel antifungal compounds 1-aryl-1-[1H-azol-1-yl($C_1$–$C_2$)alkyl]-1,3-dihydroisobenzofurans and -1,3-dihydrobenzo[c]thiophenes, 1-aryl-1-[1H-azol-1-yl-($C_1$–$C_2$)alkyl]-3,4-dihydroisochromans and -3,4-dihydroisothiochromans, pharmaceutical compositions containing them, and methods for treating fungal infections with the compounds.

SUMMARY OF THE INVENTION

The compounds of this invention are represented by the following formula I:

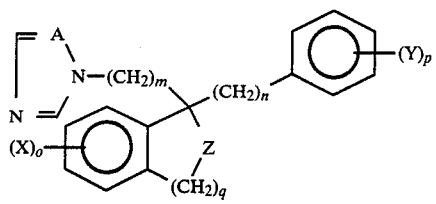

in racemic or optically active form or a pharmaceutically acceptable salt thereof; wherein A is CH or N X is independently at least one (but no more than four) of hydrogen, halogen, lower alkyl, perhaloloweralkyl, lower alkoxy, lower alkylthio,

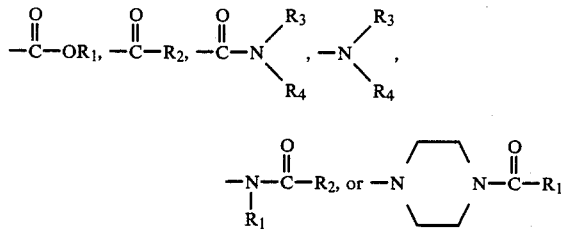

Y is independently at least one (but no more than four) of hydrogen, halogen, lower alkyl, lower perhaloalkyl, lower alkoxy, lower alkylthio,

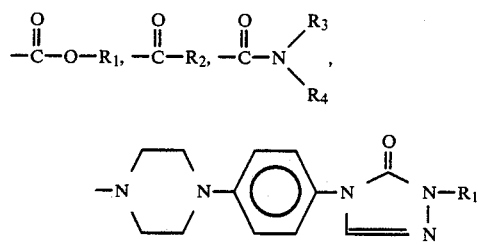

or X-substituted phenyl;

$R_1$ and $R_2$ are independently hydrogen or lower alkyl;

$R_3$ and $R_4$ are independently hydrogen, lower alkyl or when taken together with the adjacent nitrogen atom, a morpholino group, a piperazino group, a piperidino group or a pyrrolidino group;

Z is oxygen or sulfur;

m is 1 or 2 n is 0, 1 or 2 o and p are independently 1 to 4, and q is 1 or 2.

Preferred compounds represented by formula I include 1-aryl-(1H-imidazol-1-ylmethyl)-1,3-dihydroisobenzofurans, 1-aryl-(1H-1,2,4-triazol-1-ylmethyl-1,3-dihydroisobenzofurans, 1-aryl-(1H-imidazol-1-ylmethyl)-1,3-dihydrobenzo[c]thiophenes, 1-aryl-(1H-imidazol-1-ylmethyl)-3,4-dihydroisochromans, 1-aryl-(1H-1,2,4-triazol-1-ylmethyl)-3,4-dihydroisochromans, 1-aryl-(1H-imidazol-1-ylmethyl)-3,4-dihydroisothiochromans and 1-aryl-(1H-1,2,4-triazol-1-ylmethyl)-3,4-dihydroisothiochromans. The preferred aryl groups are mono- and dichlorophenyl and mono- and difluorophenyl, such as 4-chloro- and 4-fluorophenyl, 2,4-, 2,5- and 2,6-dichlorophenyl and 2,4-, 2,5 and 2,6-difluorophenyl.

The present invention also provides compounds represented by the formula II:

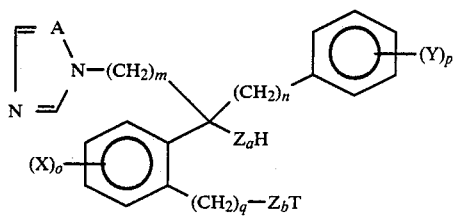

in racemic or optically active form or a pharmaceutically acceptable salt thereof, wherein A is CH or N;

X is independently at least one (but no more than four) of hydrogen, halogen, perhaloloweralkyl, lower alkoxy, lower alkylthio,

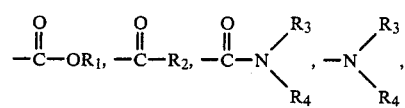

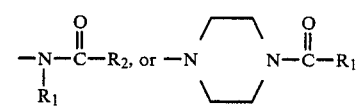

Y is independently at least one (but no more than four) of hydrogen halogen, lower alkyl, perhaloloweralkyl, lower alkoxy, lower alkylthio,

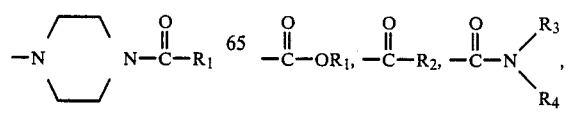

-continued

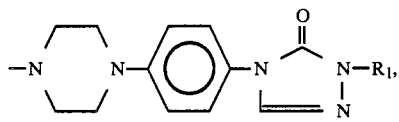  5

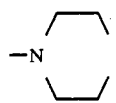  10 or X₀ substituted phenyl;

$R_1$ and $R_2$ are independently hydrogen or lower alkyl;

$R_3$ and $R_4$ are independently hydrogen, lower alkyl or when taken together with the adjacent nitrogen atom, a morpholino group, a piperazino group, a piperidino group or a pyrrolidino group;

$Z_a$ and $Z_b$ are independently oxygen or sulfur;

T is $-CH_2O(CH_2)_s-OR_1$, $$-\underset{(CH_2)_r}{\overset{-CH-O}{\diagdown}} \quad \text{or} \quad -CH_2-O-\overset{O}{\underset{\|}{C}}-R_1;$$

m is 1 or 2;
n is 0, 1 or 2;
o and p are independently 1 to 4;
q is 1 or 2;
r is 3, 4 or 5; and
s is 1, 2 or 3.

The present invention also provides a process for preparation of compounds represented by formula IIa, i.e., formula II wherein $Z_a$ and $Z_b$ are oxygen, comprising the steps of (a) contacting a compound represented by formula III, i.e.,

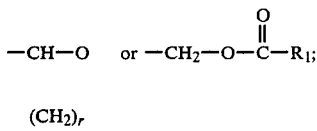

with a compound represented by formula IV, i.e.,

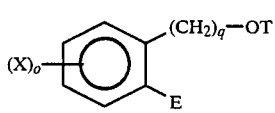

to form a compound(s) represented by formula(s) V and/or VI, i.e.,

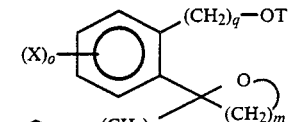 and/or

wherein

X is independently at least one (but no more than four) of hydrogen, halogen, perhaloloweralkyl, lower alkoxy, lower alkylthio, a protected carboxyl group or a protected amino group;

Y is independently at least one (but no more than four) of hydrogen halogen, lower alkyl, perhaloloweralkyl, lower alkoxy, lower alkylthio, a protected carboxyl group, a protected amino group or X-substituted phenyl;

$R_1$ and $R_2$ are independently hydrogen or lower alkyl;

$R_3$ and $R_4$ are independently hydrogen, lower alkyl or when taken together with the adjacent nitrogen atom, a morpholino group, a piperazino group, a piperidino group or a pyrrolidino group;

T is $-CH_2O(CH_2)_s-OR_1$, $$-\underset{(CH_2)_r}{\overset{-CH-O}{\diagdown}} \quad -CH_2O-\overset{O}{\underset{\|}{C}}-R_1;$$

Hal is halogen;
m is 1 or 2;
n is 0, 1 or 2;
o and p are independently 1 to 4;
q is 1 or 2;
r is 3, 4 or 5;
s is 0, 1, 2 or 3; and
e is a metal or metal halogen;

(b) contacting a compound represented by formula(s) V and/or VI with an effective amount of an imidazole or triazole compound represented by formulas VIIa and VIIb

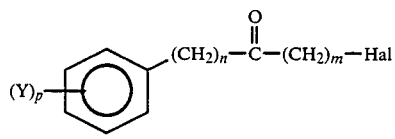 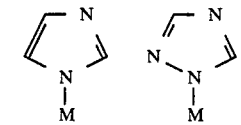

wherein M is a metal, e.g. Na or K to form a compound of formula IIa;

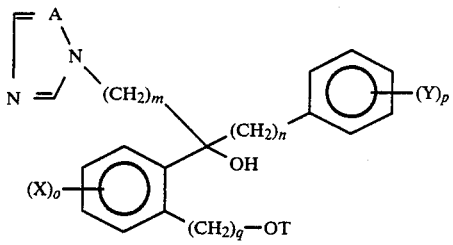

wherein

A is CH or N; and (c) recovering a compound represented by formula IIa in racemic or optically active form.

The present invention further provides a process for preparation of compounds represented by formula IIc, i.e., formula II wherein $Z_a$ is oxygen and $Z_b$ is sulfur, comprising the steps of (a) contacting a compound of formula X, i.e.,

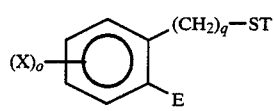

with a compound represented by formula IV, i.e.,

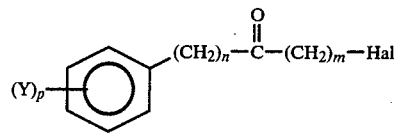

to form compounds represented by formula(s) XI and/or XII, i.e.,

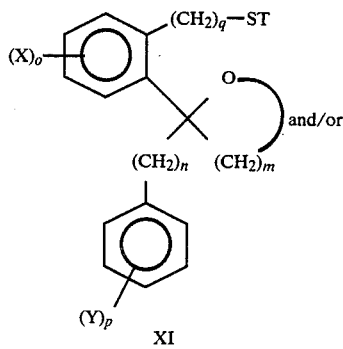

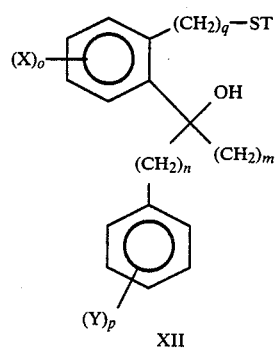

wherein

X is independently at least one of hydrogen, halogen, perhaloloweralkyl, lower alkoxy, lower alkylthio, a protected carboxyl group or a protected amino group;

Y is independently at least one of hydrogen halogen, lower alkyl, perhaloloweralkyl, lower alkoxy, lower alkylthio, a protected carboxyl group, a protected amino group or X-substituted phenyl;

$R_1$ and $R_2$ are independently hydrogen or lower alkyl;

$R_3$ and $R_4$ are independently hydrogen, lower alkyl or when taken together with the adjacent nitrogen atom, a morpholino group, a piperazino group, a piperidino group or a pyrrolidino group;

T is $-CH_2O(CH_2)_s-OR_1$,

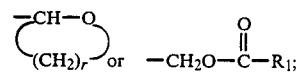

Hal is halogen;

m is 1 or 2;

n is 0, 1 or 2;

o and p are independently 1 to 4;

q is 1 or 2;

r is 3, 4 or 5;

s is 0, 1, 2 or 3; and

E is a metal or metal halogen (b) contacting a compound represented by formula(s) XI and/or XII with an effective amount of an imidazole or triazole compound represented by formulas VIIa and VIIb

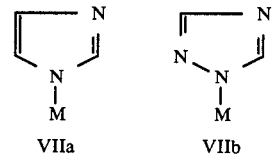

wherein

M is a metal, e.g., Na or K to form a compound represented by formula IIc;

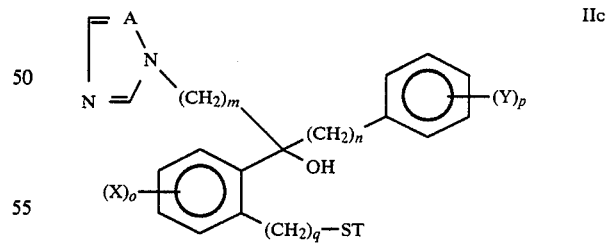

wherein A is CH or N; and (c) recovering a compound represented by formula IIc, in racemic or optically active form.

This invention also provides an antifungally effective pharmaceutical composition comprising an antifungally effective amount of a compound represented by formula I in racemic or optically active form or a pharmaceutically acceptable salt thereof, in admixture with a pharmaceutically acceptable carrier or diluent therefor.

This invention still further provides a method of treating susceptible fungal infections which comprises administering to a host in need of such treament a compound represented by formula I in racemic or optically active form or a pharmaceutically acceptable acid addition salt, or a pharmaceutical composition thereof in an amount sufficient to treat such infections.

DETAILED DESCRIPTION OF THE INVENTION

Composition of Matter Aspect

As used in the specification and claims, the term "halogen" refers to flourine, chlorine, bromine and iodine. Chlorine and fluorine are the preferred halogens. "Lower alkyl" refers to straight and branched alkyl chains of 1 to 6 carbon atoms, for example, methyl, ethyl, n-propyl, iso-propyl, n-, sec- or tert-butyl, n-, sec-, iso-, tert- or neo-pentyl, or n-, sec-, iso-, tert- or neo-hexyl groups. Methyl and ethyl are preferred lower alkyl groups. "Lower perhaloalkyl" refers to straight and branched alkyl chains of 1 to 6 carbon atoms wherein each hydrogen is replaced by a halogen as defined hereinabove, preferably by fluorine and/or chlorine. Trifluoromethyl is prefered. "Lower alkoxy" in its alkyl portion refers to straight and branched chain alkyl groups of 1 to 6 carbon atoms, e.g., methoxy, ethoxy, isopropoxy, t-butoxy, isopentoxy or n-hexoxy. Methoxy is preferred. "Lower alkylthio" in its alkyl portion refers to straight and branched alkyl groups of 1 to 7 carbon atoms, i.e., methylthio, ethylthio, propylthio, butylthi, hexylthio, heptylthio, Methylthio and ethylthio are preferred lower alkyl thio groups.

Preferred "X" groups, are hydrogen, chlorine, flourine, methyl, ethyl, trifluoromethyl, methoxy, methylthio,

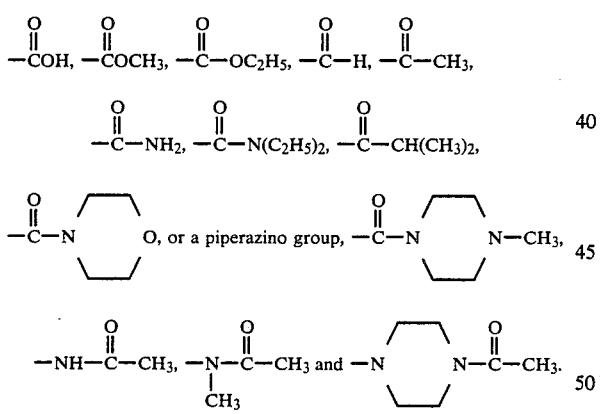

Hydrogen and monochlorine or monofluorine are most preferred

Preferred "Y" groups are the "X" groups as defined herein and $(X)_o$-substituted phenyl including phenyl, or phenyl substituted by at least one but no more than four groups such as mono, di, tri, and tetrahalophenyl, mono-, di-, tri-, and tetra-substituted lower alkylphenyl; mono-, di-, tri-, and tetraperhaloloweralkyl substituted phenyl; mono-, di-, tri-, and tetra-substituted lower alkyl thiophenyl; phenyl substituted by one to four of

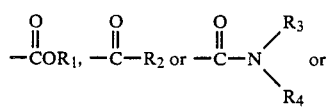

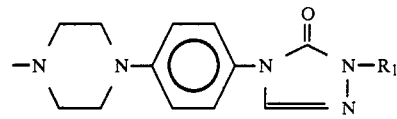

wherein $R_1$-$R_4$ are defined herein for formula I.

Most preferred "Y" groups are mono- and dichlorine or mono- and difluorine.

$Z_a$ is oxygen or sulfur, preferably oxygen. A is CH or N. While m may be 1 or 2, m is preferably 1. The letter n may be 0 or 1 but is preferably 0.

The term "protected amino group" as used herein means an amino group substituted with one of the commonly-employed amino blocking groups which is compatible with other functional groups present in the compounds of the invention represented by formulas I and II, is substantially non-reactive with organometallics especially organolithium, organosodium and organomagnesium reagents and is readily removeable to provide the amino group under reactive conditions that do not adversely affect the structure of the compounds of the invention. Typically suitable amino blocking groups include N-lower alkoxycarbonyl, e.g., N-methoxycarbonyl, N-loweralkenyl, e.g., N-allyl, N-loweralkoxyloweralkyl, e.g., N-methoxymethyl, N-arylalkoxyalkyl, e.g., benzyloxymethyl, N-triaryllower-alkyl, e.g., N-triphenylmethyl, N-triloweralkylsilyl, e.g., N-trimethylsilyl and N-tetraloweralkyldisilyl alkylene, e.g.,

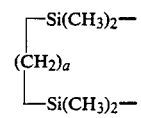

wherein a is 2 or 3 but preferably a is a 2. The preferred amino blocking group is

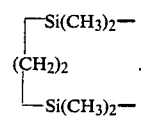

The compounds of the present invention represented by formulas I and II and independently substituted by X equal to

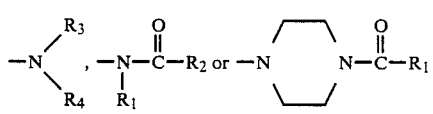

or independently substituted by Y equal to

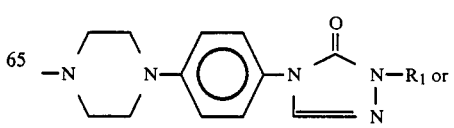

-continued

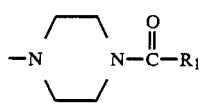

are prepared in accordance with the process aspects of the present invention a.e., preparation of compounds of the present invention having the protected amino group. The protected amino group is conveniently converted into the free or deprotected amino group by use of, for example, aqueous mineral acids. The deblocked amino group is converted into

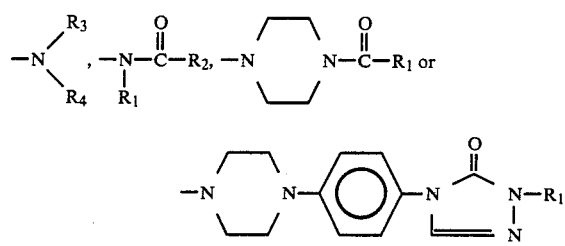

by standard synthetic chemical techniques well known to those skilled in the art. See for example, "Compendium of Organic Synthetic Methods", by I. T. Harrison and Shuyen Harrison, Wiley-Interscience, N.Y., N.Y. 1971, pages xi, 213–218, 240–248 and 260.

The term "protected carboxyl group" as used herein means a carboxyl group substituted with one of the commonly-employed carboxyl blocking groups which is compatible with the functional groups present in the compounds of the invention represented by formulas I and II, is substantially non-reactive with organometallics, especially organolithium, organosodium and organomagnesium reagents and is readily removeable to provide the carboxyl group under reaction conditions that do not adversely affect the structure of the compounds of the invention. By the term "substantially non-reactive" as used in the specification is meant that the protected carboxyl group shows low or no reactivity in the presence of the above organometallic reagents. Generally the carboxyl groups are protected as 2-alkyl-1,3-oxazolines with 2-alkyl-4,4-diloweralkyl-1,3-oxazolines being preferred; the 2-alkyl-4,4-dimethyl-1,3-oxazolines represented by formula:

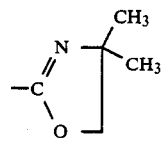

are more preferred.

The compounds of the present invention represented by formulas I and II are independently substituted by X or Y equal to

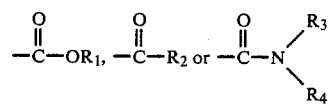

are prepared in accordance with the process aspects of the present invention, i.e., preparation of compounds of the present invention having the protected carboxyl group. The protected carboxyl group is conveniently converted into the free or deblocked carboxyl group by use of, for example, aqueous mineral acids. The deblocked carboxyl group is converted into

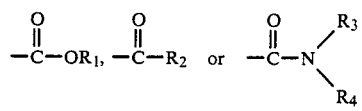

wherein $R_1$, $R_2$, $R_3$ and $R_4$ are defined as above, by standard synthetic chemical reactions well known to those skilled in the art. See for example "Compendium of Organic Synthetic Methods" by I. T. Harrison and Shuyen Harrison, Wiley-Interscience, N.Y., N.Y., 1920, pages xi, 204–207, 272–279 and 380–386.

Compounds of formula I and II within the scope of this invention can exist in the form of racemic mixtures of the optically active isomers thereof and as the individual optically active isomers which can be obtained by standard techniques, e.g. resolution of the racemic mixtures.

Compounds of this invention represented by formulas I and II are prepared by the following procedures.

PROCEDURE A

Preparation of compounds represented by formula I wherein $Z=O$; $q=1$ or 2; $n=0$ or 1 and $m=1$ or 2 and of compounds represented by formula IIa, i.e., formula II wherein $Z_a=Z_b=O$ and q, n and m are as defined for I A compound represented by formula III is reacted in an aprotic organic solvent with approximately an equimolar amount of a compound represented by formula IV to give a mixture of compounds represented by formulas V and/or VI:

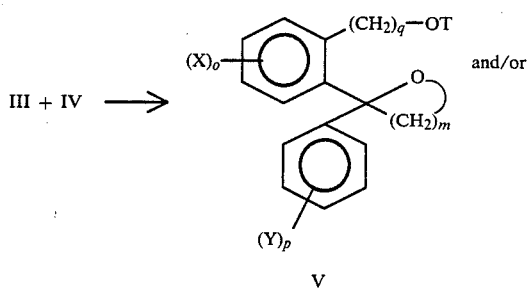

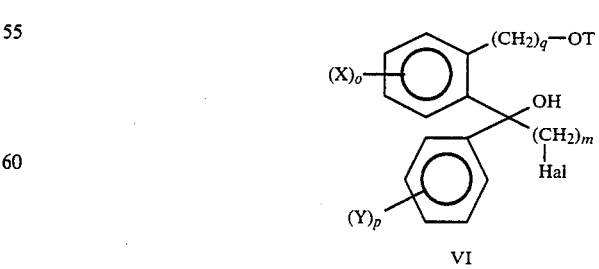

wherin Hal is halogen, e.g., Br or Cl; and T is an acidlabile hydroxy protecting group, e.g., $-CH_2-O(CH_2)_2-OCH_3$

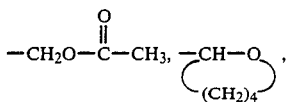

i.e., 2-tetrahydropyranyl (THP), and the like when E is MgHal, e.g., MgBr or T is, for example, THP or Li when E is Li. Generally, E may be any metal or metal halogen, e.g., Li, ZnHal or MgHal which provides an organometallic compound III which reacts with the carbon of the carbonyl moiety in IV to form V and/or VI. Reaction of III and IV produces V or VI alone or mixtures of V and VI depending on many factors including value of m the steric size of the aryl groups, nucleophilicity of halogen, the reaction solvent and other reaction conditions. Compounds having formulas III and IV are known.

The mixture of the compounds having formula(s) V and/or VI is treated with an effective amount, i.e., from about 1 to 4 equivalents of an imidazole or triazole compound of formula VIIa or VIIb (M is Na or K) in a liquid medium for a time sufficient to form the compound represented by formula IIa

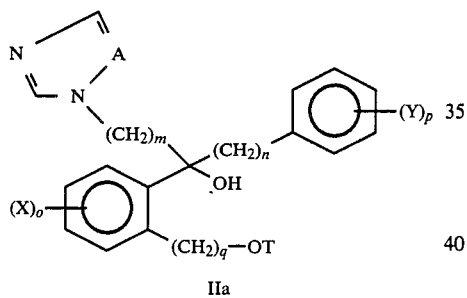

wherein A is CH when compound VIIa is used and A is N when compound VIIb is used.

Typical suitable liquid media include aromatic hydrocarbons, e.g., benzene, toluene, xylenes; ethers, e.g., dioxane, tetrahydrofuran (THF) or dimethoxyethane (DME); aprotic solvents, e.g., acetonitrile, dimethylformamide (DMF), dimethylacetamide, dimethylsulfoxide (DMSO). DMF is preferred. The reaction mixture of V and/or VI and VIIa or VIIb is heated at a temperature of from about 0° C. to the reflux temperature of the reaction mixture for about 1 to 6 hrs, preferably at about 90° C. for about 1-2 hrs.

Compounds of formula I are obtained by heating compounds of formula IIa with an aqueous mineral acid, e.g., 6N HCl for 1-4 hrs. In the embodiment of the present invention wherein a protected carboxyl group, preferably

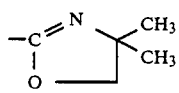

or a protected amino group, preferably

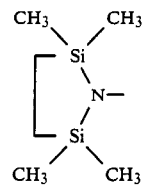

is present in IIa, such treatment of IIa with aqueous mineral acid provides the free carboxyl or free amino groups. The crude form of the compound of formula I thereby produced is isolated and purified utilizing known techniques such as basification, extraction, chromatography and recrystallization.

Procedure A is particularly suitable for preparation of compounds represented by formula I and IIa wherein $m=1$.

PROCEDURE B

Preparation of compounds of Formula I wherein $Z=O$; $q=1$ or 2; $n=0$ or 1, $m=2$; and of compounds represented by formula IIb, i.e., formula II wherein $Z_a=Z_b=O$ and $q=1$ or 2; $n=0$ and $m=2$ A compound represented by formula III is reacted in an aprotic organic solvent with approximately an equimolar quantity of the compound represented by formula VIII to give a compound represented by formula IIb:

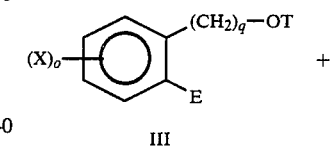

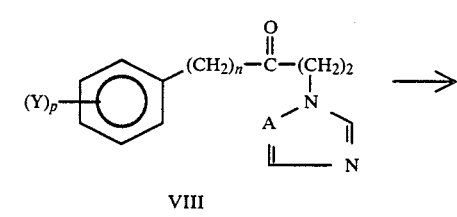

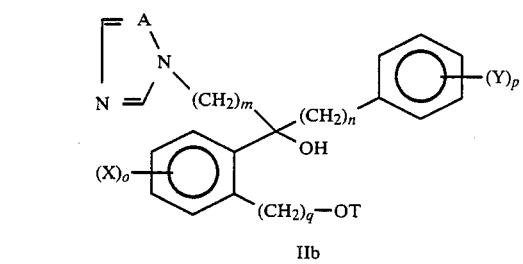

Compound IIb is heated with an aqueous mineral acid e.g., 6N HCl for about 1-4 hrs to form a compound represented by formula I wherein $Z=O$; $q=1$ or 2; $n=0$ or 1; and $m=2$ Compound VIII is prepared by reacting a compound having formula IX, i.e.

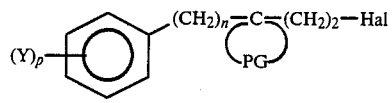

wherein PG is a suitable protecting group for the carbonyl moiety, e.g., dioxolane, with an effective amount, i.e., from about 1 to 4 equivalents of compound VIIa or VIIb in an aprotic organic solvent.

PROCEDURE C

Preparation of compounds of formula I wherein Z=S; q=1 or 2; n=0 or 1, and m=1 and of compounds represented by IIc, i.e., II wherein $Z_a$=O and $Z_b$=S, q=1 or 2, n=0 or 1 and m=1

A compound represented by formula X is contacted with an approximately equimolar amount of a compound represented by the formula IVa in accordance with the procedure as described in Procedure A hereinabove to provide compounds of formulas XIa and/or XIIa

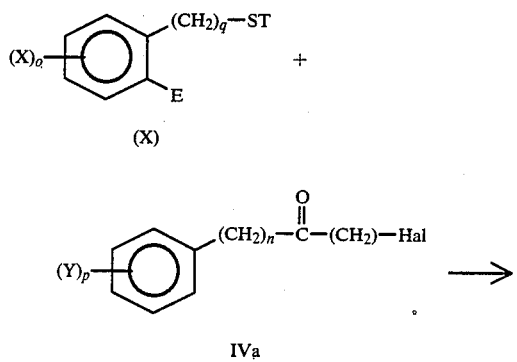

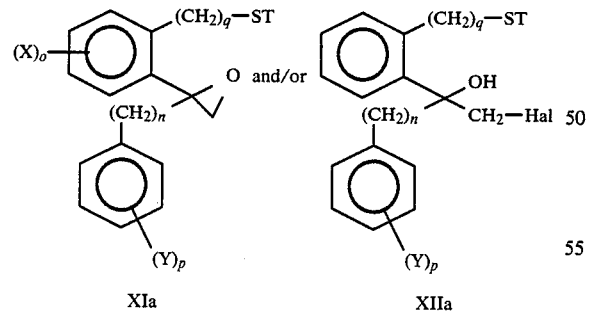

Compound IId, i.e., II wherein $Z_a$=O and $Z_b$=S, q=1 or 2; n=0 or 1 and m=1 are prepared by reaction of XIa and/or XIIa with compound VIIa or VIIb in accordance with procedure of A

XIa and/or XIIa + VIIa or VIIb ⟶

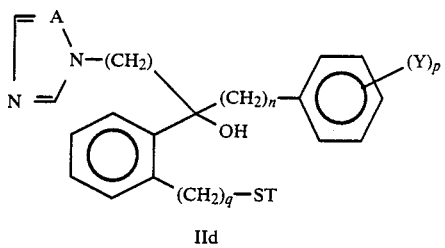

Compound I wherein Z=S, q=1 or 2 and n=0 or 1 and m=1 is prepared by refluxing IId in 6N HCl for about 1-6 hrs.

PROCEDURE D

Preparation of compounds represented by formula I wherein Z=S, q=1 or 2, n=0 or 1 and m=2 and compounds IIe wherein $Z_a$ is oxygen and $Z_b$ is sulfur and q=1 or 2, n=0 or 1 and m=2

Compound X is reacted with compound VIII to give compound IIe

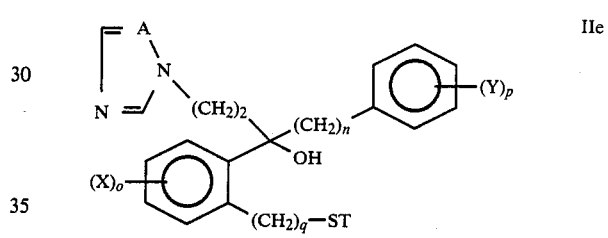

Compound I wherein Z=S, q=1 or 2; n=0 or 1 and m=2 are prepared by refluxing IIe in 6N HCl for about 1-6 hours.

Compounds of formula X are prepared by contacting a hydroxy compound represented by formula XIII wherein T is hydrogen with an excess of a stoichiometric amount of a halogenating reagent, e.g., $PX_3$, $SOX_2$ wherein X is Cl or Br to form the corresponding halide which is converted into the mercaptan X by conventional reactions.

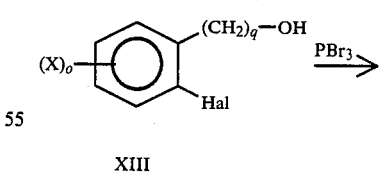

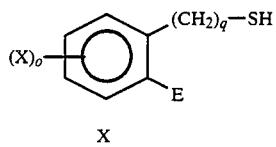

X

PROCEDURE E

Preparation of compounds of Formula I wherein Z=O; q=1; n=0 or 1; and m=1 or 2: alternate to procedure A A compound represented by formula XIV, i.e.,

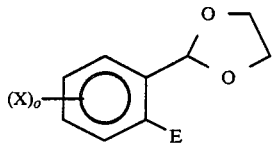

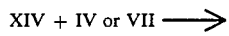

is reacted in a suitable aprotic organic solvent, e.g., THF, with approximately an equimolar amount of a compound represented by formula IV or VII to give, respectively, a mixture of XV and/or XVI:

XIV + IV or VII ⟶

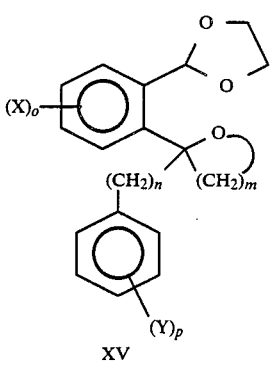

XV and/or

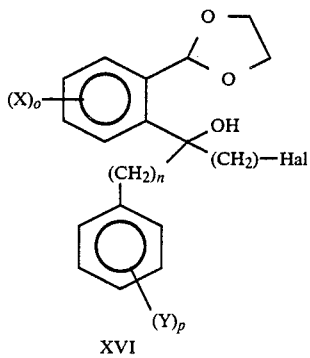

XVI

The reaction of XIV and IV or VII produces XV or XVI alone or mixtures of XV and XVI depending on many factors including the value of m, the size of the aryl groups, the nucleophilicity of halogen, the reaction solvent, temperature and other reaction conditions.

The mixture of compounds having formula(s) XV and/or XVI is treated with an effective amount, i.e., about 1 to 4 mole equivalents of an azole salt of formula VIIa or VIIb in a suitable liquid medium, e.g., DMF, for a time sufficient to form the compound represented by formula XVII:

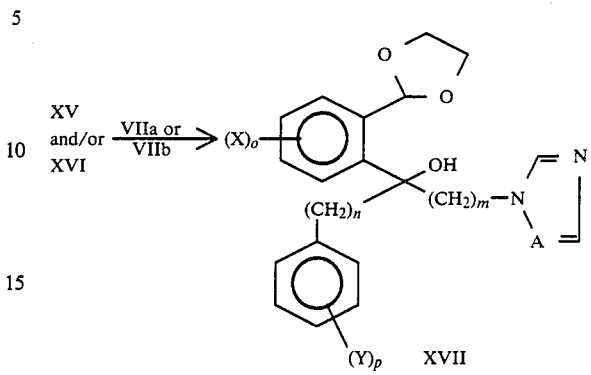

XVII

A compound represented by formula XVII is heated with an aqueous mineral acid, e.g., 2-6N HCl, or with a suitable aqueous organic acid, e.g., 2-20% aqueous oxalic acid for about 1 to 24 hrs. The resulting mixture is rendered basic, and the product represented by formula XVIII is isolated and purified utilizing known techniques such as extraction, chromatography, and crystallization.

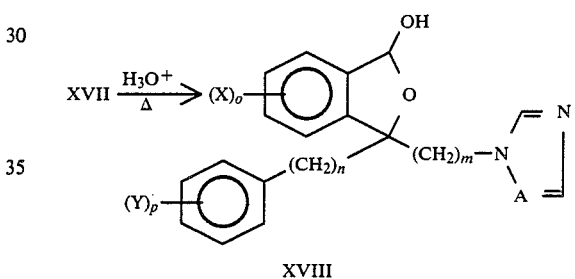

XVIII

The compound represented by formula XVIII is reacted in a suitable solvent with 1 to 20 molar equivalents of a suitable reducing agent, conveniently sodium borohydride at temperatures from about 20° C. to the reflux temperature (preferably at ambient temperature) of the reaction mixture, for a sufficient time (generally about 2-24 hours) to form the compound represented by formula XIX. Suitable solvents include water, lower alcohols, and mixtures of both; aqueous ethanol is the preferred solvent.

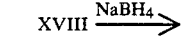

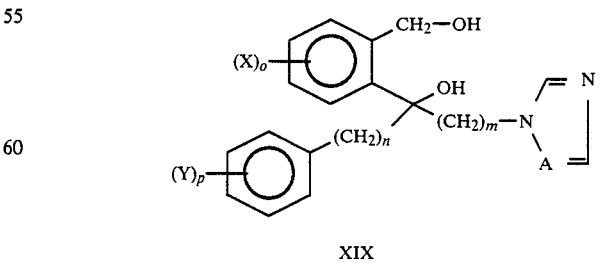

XIX

Compounds of formula I wherein q=1 are obtained by heating compounds of formula XIX with an aqueous mineral acid, e.g. 6N HCl for about 1-4 hrs. The crude form of the compound of formula I thereby produced is isolated and purified as described in procedure A.

PHARMACEUTICAL COMPOSITION AND METHOD-OF-USE ASPECTS OF THE INVENTION

The present invention contemplates a method of treating susceptible fungal infections in a host, e.g., animals, especially a warm blooded animal such as humans containing or subject to attack by fungi, which comprises administering to said host in need of such treatment a compound of formula I or a pharmaceutical composition thereof in an amount sufficient to treat such infections.

Typical suitable pharmaceutically acceptable salts are nontoxic acid addition salts formed by adding to the compounds of this invention a stoichiometric amount of mineral acid such as HCl, HBr, HNO$_3$, H$_2$SO$_4$ or H$_3$PO$_4$ or an organic acid, such as acetic, propionic, valeric, oleic, palmitic, stearic, lauric, benzoic, lactic, para-toluene sulfonic, methane sulfonic, citric, maleic, fumaric, succinic and the like. respectively.

These salts may be obtained by employing conventional procedures such as, for example, by mixing solutions containing stoichiometric amount of the free base (I) and the desired acid together, followed by filtration to collect the required salt, if insoluble, or by evaporation of the solvent from the system in accordance with standard techniques.

The compounds of formula I exhibit in vitro antifungal activity against human and animal pathogens such as the following: Aspergillus, various strains of Candida, Epidermophyton, Microsporum, Monosporium and Trichophyton.

The in vitro antifungal activity tests were performed via conventional agar dilution methods in Sabouraud broth and Eagles media.

In the Sabouraud broth (SAB) medium, for example, 1-(4-chlorophenyl)-1-(1H-1,2,4-triazol-1-ylmethyl)-1,3-dihydroisobenzofuran-hydrochloride showed activity against a large number of fungi, for example against *Epidermophyton floccosum*, and *Trichophyton mentagrophytes* and *rubrum*, *Microsporum canis* and against *Candida parapsilosis*; the minimum Inhibitory Concentration (MIC) in the SAB medium ranged from about <0.031 to about 1.0 mcg/ml in 48 and 72 hrs tests. In Eagles medium, this compound was tested against various strains of Candida, e.g., *C. albicans, C. tropicalis* and *C. stellatoidea* and the MIC in each was determined to be about <0.031 mcg/mL after 48 hour tests.

In the Sabourand broth medium, for example 1-(4-chlorophenyl-1-(1H-imidazol-1-ylmethyl)-1,3-dihydroisobenzofuran hydrochloride showed anti-fungal activity against *Epidermophyton floccosum, Candida parapsilosis, Aspergillus niger, Trichophyton mentagrophytes* (Da480) and *-rubrum*, and *Microsporum Canis* with MICs ranging from about <0.031 to about 4.0 mcg/mL after 48 and 72 hour tests; In the Eagles medium, the MIC of this compound against various strains of Candida, e.g., *C. albicans, C. tropicalis* and *C. stellatoidea* was found to be about <0.031 mcg/ml after 48 hour tests.

The compounds of this invention and their pharmaceutically acceptable salts are particularly effective as topical antifungal agents as demonstrated by in vivo tests in animals, e.g. a hamster vaginal Candida infection model, and a guinea pig, dermatophyte infection model. These tests indicate the compounds of this invention to be broad-spectrum antifungal agents active against dermatophyte and vaginal yeast infections when administered topically.

In general, the dosage of compounds of formula I administered to combat a given fungal infection is similar to the dosage requirements of the present commerical products miconazole, clotrimazole, and ketoconazole.

In general, the topical dosage range will be from about 0.1% to about 10% by weight of a particular pharmaceutical composition formulated in single or divided doses, with the preferred range being about 0.5% to about 4% and with the most preferred range being about 1% to about 2%.

It will be appreciated that the actual preferred dosages of the compounds of this invention or pharmaceutically acceptable salts thereof will vary according to the particular compound being used, the particular compositions formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

This invention also contemplates antifungally effective pharmaceutical compositions comprising an antifungally effective amount of a compound of formula I or its pharmaceutically acceptable salts in admixture with a pharmaceutically acceptable, non-toxic carrier adapted for topical, oral or parenteral use. The preferred mode of administration is topical.

Topical dosage forms may be prepared according to procedures well known in the art, and may contain a variety of ingredients. The formulations for topical use include ointments, creams, lotions, powders, aerosols, vaginal tablets, pessaries and sprays. Of these, ointments, lotions and creams may contain water, oils, fats, waxes, polyesters, alcohols, or polyols, plus such other ingredients as fragrances, emulsifiers and preservatives. Powders are made by mixing the active ingredient with a readily available, inert, pulverous distributing agent, such as talcum, calcium carbonate, tricalcium phosphate, or boric acid. Aqueous suspensions of the above powders may also be made. Solutions or emulsions may also be prepared using inert solvents which are preferably nonflammable, odorless, colorless and non-toxic, for example vegetable oils, isopropanol, dimethyl sulfoxide, hydrogenated naphthalenes, and alkylated naphthalenes. Similarly, aerosol or non-aerosol sprays may be prepared using solutions or suspensions in appropriate solvents e.g., difluorodichloromethane for aerosols.

In the case of topical formulations, e.g., ointments, creams, lotions, powders, tablets, pessaries or sprays, the formulation will contain about 0.1 to 10 grams of a compound of formula I per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously are usually in the form of a sterile solution, and may contain salts or glucose to make the solution isotonic.

The following examples illustrate the invention:

EXAMPLES

EXAMPLE 1

2-BROMO-4,6-DICHLOROBENZYL ALCOHOL

A.

2-BROMO-4,6-DICHLOROTOLUENE

To a mixture of 32 g of 4,6-dichlorotoluene and 0.3 g of anhydrous $FeCl_3$, add, with stirring, 10 g of bromine in 1 g portions while maintaining a temperature of 20°–25° C. Add thereto a solution of 22 g of bromine in 100 mL of $CCl_4$ slowly while maintaining a temperature of 20°–25° C. After the addition of bromine is complete, stir the mixture so formed for 15 min, and dilute the reaction mixture with 200 mL of $CH_2Cl_2$, and wash the organic solution with 5% aqueous sodium thiosulfate. Dry the organic layer over anhydrous $K_2CO_3$, filter, and evaporate to a residue. Recrystallize the residue from $CH_3CN$ to give 32 g of 2-bromo-4,6-dichlorotoluene, mp 84°–5° C.

B.

2-BROMO-4,6-DICHLOROBENZYL BROMIDE

Stir slowly, an intimate mixture of 220 g of 2-bromo-4,6-dichlorotoluene, 167 g of N-bromosuccinimide and 1 g of benzoyl peroxide in a flask (equipped with a condenser and stirrer) immersed in an 145° C. oil bath. After 10–20 min a vigorous eruption occurs and the mixture liquifies. Remove the oil bath and stir for an additional 5 min. Add 1.5 L of $CCl_4$ slowly through the condenser. Cool the mixture and suction filter the resulting reaction mixture. Wash the filtrate with 5% aqueous sodium thiosulfate, dry over anhydrous $K_2CO_3$, filter and evaporate to a residue. Fractionally distill the residue to give 134 g of 2-bromo-4,6-dichlorobenzyl bromide, bp 94°–97° C. (0.2 tor).

C.

2-BROMO-4,6-DICHLOROBENZYL ALCOHOL

Heat a mixture of 22 g of 2-bromo-4,6-dichlorobenzyl bromide, 30 g anhydrous sodium acetate and 80 mL of glacial acetic acid for 18 hr at 100° C. Evaporate the mixture to a dry residue. Treat the residue with 200 mL of ethanol and 200 mL of 2N NaOH. Stir the mixture at reflux for 3 hr. Cool the mixture and concentrate the cooled mixture to 50 mL. Extract the cooled concentrate with $Et_2O$. Dry the extract over anhydrous $K_2CO_3$ and evaporate it to a dry residue. Recrystallize the residue from toluene-hexane to give 10 g of 2-bromo-4,6-dichlorobenzyl alcohol, mp 111°–112° C.

EXAMPLE 2

2-BROMOBENZYL-(2-TETRAHYDROPYRANYL)ETHER

To a solution of 25 g of 2-bromobenzyl alcohol in 400 mL of $CH_2Cl_2$ at 10° C., add 0.25 g of p-toluenesulfonic acid, and then add 17 g of dihydropyran in one portion. Stir the solution for 30 min at ambient temperature. Wash the solution with 5% aqueous $K_2CO_3$ and then saturated brine, and dry over anhydrous $K_2CO_3$. Filter the mixture, evaporate the filtrate, and fractionally distill to give 33 g of 2-bromobenzyl-(2-tetrahydropyranyl)ether, bp 119°–122° C. (0.8 tor)

EXAMPLE 3

2-BROMO-4,6-DICHLOROBENZYL-(2-TETRAHYDROPYRANYL)ETHER

Treat the title compound of Example 1C in a manner exactly analogous to the procedure of Example 2. Isolate the title compound by chromatography.

$^1H$ NMR $(CDCl_3)\delta$: 1.4–1.9 (m, 6H), 3.4–4.0 (m, 2H), 4.6 (q, 2H), 4.7 (m, 1H), 7.4 (s, 1H), 7.8 (s, 1H).

EXAMPLE 4

1-PHENYL-1-(1H-IMIDAZOL-1-YLMETHYL)-1,3-DIHYDROISOBENZOFURAN HYDROCHLORIDE

A.

1-PHENYL-1-[2-[(2-TETRAHYDROPYRANYL)OXY]METHYL]PHENYL OXIRANE

Prepare the Grignard reagent by adding 6 g of the title compound of Example 2 to 0.54 g of magnesium in 10 mL of tetrahydrofuran (THF). Add the Grignard reagent so formed dropwise over a period of 15 min at 0°–5° C. to a solution of 3.25 g of phenacyl chloride in 100 mL of THF. Allow the solution to warm to room temperature, and stir for 18 hr. Cool the reaction mixture to 0° C. Vigorously stir the cooled reaction mixture and add 50 mL of saturated aqueous $NH_4Cl$. Separate the aqueous layer and extract with ethyl acetate (EtOAc), and wash the combined THF-EtOAc extracts with saturated brine and dry over anhydrous $Na_2SO_4$. Filter the mixture and evaporate the filtrate to leave 7.4 g of crude 1-phenyl-1-[2-[(2-tetrahydropyranyl)oxy]methyl]phenyl oxirane.

$^1H$ NMR $(CDCl_3)\delta$: 1.3–2.0 (m, 6H), 3.1–3.8 (m), and 3.3 (q), [4H total] 4.5–4.8 (m, 3H), 7.1–7.8 (m, 9H).

B.

2-[(1H-IMIDAZOL-1-YL)-1-PHENYL-1-[2-[(2-TERTAHYDROPYRANYL)OXY]METHYL]PHENYL ETHANOL

Add crude oxirane of Example 4A in 10 mL of THF to a stirred suspension at 20° C. of 4.4 g of imidazolesodium (prepare by mixing 1.2 g of NaH and 3.4 g of imidazole at 5°–20° C.) in 50 mL of DMF. Heat the mixture for 2 hr on a steam bath. Pour the resulting mixture over water-ice and stir. Suction filter the mixture to leave a precipitate. Extract the filtrate with ethyl acetate (EtOAc). Wash the extract with brine and dry over anhydrous $Na_2SO_4$. Dry the precipitate in a vacuum dessicator at room temperature. Evaporate the EtOAc to give residue. Triturate the residue with EtOAc and combine the remaining solid with the dried precipitate and wash with EtOAc to leave 4.7 g of crude 2-(1H-imidazol-1-yl)-1-phenyl-1-[2-[(2-tetrahydropyranyl)oxy]methyl]phenylethanol.

$^1H$ NMR $(CDCl_3)$ $\delta$: 1.3–2.0(m, 6H), 3.3–3.9(m, 2H), 4.1(q, 2H), 4.4(m) and 4.8(q), [3H total], 5.8(s, 1H), 6.6(s, 1H), 6.8(s, 1H), 7.0–7.8(m, 10H).

C.

1-PHENYL-1-(1H-IMIDAZOL-1-YLMETHYL)1,3-DIHYDROISOBENZOFURAN HYDROCHLORIDE

Heat the crude alcohol from Example 4B at reflux in 50 mL of 6N hydrochloric acid for 1.5 hr. Pour the hot reaction mixture into a mixture of 90 mL of 3N NaOH, 100 mL of a 10% K₂CO₃ solution and 100 g of ice. Extract the mixture with CHCl₃. Dry the extract over anhydrous Na₂SO₄, filter and evaporate to a residue. Chromatograph the residue on silica gel eluting with CH₂Cl₂—EtOAc to afford 3.3 g of a solid product. Dissolve the product in ethyl ether and treat the solution with dry HCl. Evaporate the resulting mixture to leave a solid. Recrystallize the solid from CH₃CN to leave 2.2 g of the title compound, mp 209°–212° C.

EXAMPLE 5

1-(4-CHLOROPHENYL)-1-(1H-IMIDAZOL-1-YLMETHYL)-1,3-DIHYDROISOBENZOFURAN HYDROCHLORIDE

A.

1-(4-Chlorophenyl)-1-[2-[(2-tetrahydropyranyl)oxy]methyl]phenyl oxirane is prepared from 1-(2bromobenzyl-(2-tetrahydropyranyl)ether and 4-chlorophenacyl chloride in accordance with procedure of Example 4A.

$^1$H NMR (CDCl₃) δ: 1.3–2.0(m, 6H)3.1–3.8(m) and 3.3(q), [4H total], 4.5–4.8(m, 3H), 7.0–7.9(m, 8H).

B.

1-(4-Chlorophenyl)-2-(1H-imidazol-1-yl)-1[2-[(2-tetrahydropyranyl)oxy]methyl]phenylethanol is prepared from the title compound of Example 5A in accordance with procedure of Example 4B.

$^1$H NMR (CDCl₃) δ: 1.3–2.0(m, 6H), 3.2–3.8(m, 2H), 4.1(q, 2H), 4.3(m) and 4.8(q)[3H total], 5.0(s, 1H), 6.5(s, 1H), 6.7(s, 1H), 7.0–8.0(m, 8H)

C.

1-(4-Chlorophenyl)-1-(1H-imidazol-1-ylmethyl)-1,3-dihydroisobenzofuran hydrochloride, mp 192°–193° C. is prepared form title compound of Example 5B in accordance with the procedure of Example 4C.

EXAMPLE 6

1-(2,4-DICHLOROPHENYL)-1-(1H-IMIDAZOL-1-YLMETHYL) 1,3-DIHYDRO-4,6-DICHLOROISOBENZOFURAN HYDROCHLORIDE

A.

1-(3,5-DICHLORO-2-HYDROXYMETHYL-PHENYL)-1-(2,4-DICHLOROPHENYL)OXIRANE

To a solution of 25 g of 2-bromo-4,6-dichlorobenzyl alcohol in 250 mL of THF at −65° to −70° C., add 132 mL of 1.6M n-butyllithium in hexane over 2 hr. Add a solution of 22 g of 2,4-dichlorophenacyl chloride in 75 mL of THF rapidly and stir the reaction mixture for an additional 20 min without further cooling. Cool the reaction mixture to 5° C., and add thereto 350 mL of 5% aqueous K₂CO₃ (with vigorous stirring). Extract the aqueous layer with CH₂Cl₂. Dry the combined THF—CH₂Cl₂ extracts over anhydrous K₂CO₃, filter and evaporate in vaccuo to give a residue. Chromatograph the residue on silica gel and elute with EtOAc-CH₂Cl₂ to afford 9.1 g of crude 1-(3,5-dichloro-2-hydroxymethylphenyl)-1-(2,4-dichlorophenyl)oxirane.

$^1$H NMR (CDCl₃) δ: 3.3(m, 2H), 4.7(s, 2H), 7.3(m, 3H), 7.7(d, 1H), 8.0(s, 1H).

B.

1-(3,5-DICHLORO-2-HYDROXYMETHYL-PHENYL)-1-(2,4-DICHLOROPHENYL)-2-(1H-IMIDAZOL-1-YL)ETHANOL

Add a solution of the crude oxirane from Example 6A in DMF to a solution of 4.4 g of imidazolesodium in 120 mL of DMF. Heat the resulting mixture, with stirring at 85° C. for 2 hr. Cool and evaporate the reaction mixture to a residue. Partition the residue with water and EtOAc. Evaporate the EtOAc extract to a residue. Chromatograph the residue on silica gel eluting with acetone-EtOAc to afford 4.7 g of the title compound, mp 208°–211° C.

C.

1-(2,4-DICHLOROPHENYL)-1-(1H-IMIDAZOL-1-YLMETHYL)-1,3-DIHYDRO-4,6-DICHLOROISOBENZOFURAN HYDROCHLORIDE

Heat 3 g of the alcohol of Example 6B at reflux in 100 mL of 6N hydrochloric acid for 2.5 hr. Cool the resulting mixture. Basify the mixture with 3N NaOH and extract the basified mixture with CH₂Cl₂. Dry the CH₂Cl₂ extracts over anhydrous Na₂SO₄, filter and evaporate to a residue. Chromatograph the residue on silica gel eluting with EtOAc. Combine the product-bearing fractions and concentrate to 500 mL. Treat the concentrated fractions with ethereal HCl. Concentrate the liquor so formed to afford the title compound as a crystalline solid, mp 200°–203° C.

EXAMPLE 7

1-[(4,1'-BIPHENYL]YL]-1-(1H-IMIDAZOL-1-YLMETHYL)1,3-DIHYDROISOBENZOFURAN HYDROCHLORIDE

The title compound, a tan solid having mp 221°–224° C., is prepared in accordance with the procedures of Example 5 except that in procedure 5A an equivalent amount of 4-phenylphenacyl-chloride is substituted for 4-chlorophenacyl chloride.

EXAMPLE 8

1-(4-CHLOROPHENYL)-1-(1H,-1,2,4-TRIAZOL-1-YLMETHYL)-1,3-DIHYDROISOBENZOFURAN HYDROCHLORIDE

A.

2-[2-[(4-CHLOROPHENYL)OXIRANYLMETHYL]PHENYL]-1,3-DIOXOLANE

Prepare the Grignard reagent from 16 g of 2-(2-bromophenyl)-1,3-dioxolane and 1,7 g of magnesium in 150 mL of THF. Add the Grignard reagent so formed dropwise over 30 min at 0°–5° C. to a solution of 14.9 g of 4-chlorophenacyl bromide in 150 mL of THF. Stir the reaction mixture for an additional 30 min at 0°–5° C. Add 4 g of NH₄Cl and 200 mL of saturated brine with vigorous stirring and warm the reaction mixture so formed to 20° C. Separate the aqueous layer and extract with EtOAc. Wash the combined THF-EtOAc extracts with brine, dry over anhydrous Na₂SO₄, and filter and evaporate to give a residue. Chromatograph the residue on silica gel eluting with EtOAc-hexane (1%Et₃N) to afford 13 g of the title compound: $^1$H NMR (CDCl₃) δ: 3.3(q, 2H), 4.0(m, 4H), 6.0 (s, 1H), 7.0–7.7(m, 8H).

B.
1-(4-CHLOROPHENYL)-1-[2-[2-(1,3-DIOXOLANYL)]PHENYL]-2-(1H-1,2,4-TRIAZOL-1-YL)ETHANOL

Heat, with stirring, a mixture of 13.3 g of the title compound of Example 7A, and 1H-1,2,4-triazolesodium (from 7.2 g 1H-1,2,4-triazole and 2.4 g NaH) in 200 mL of DMF at 60° C. for 6 hr. Pour the resulting reaction mixture into water-ice and extract with EtOAc. Wash the extract with water, then brine, dry over anhydrous $Na_2SO_4$, filter, and evaporate to give a residue. Chromatograph the residue on silica gel eluting with acetone-$CH_2Cl_2$. Dissolve the crude product recovered in hot $CH_3CN$, treat with charcoal, filter, and evaporate. Wash the residue with $Et_2O$ and dry to leave 10.8 g of the title compound, mp 161°–163° C.

C.
3-(4-CHLOROPHENYL)-3-(1H-1,2,4-TRIAZOL-1-YLMETHYL)-1,3-DIHYDROISOBENZOFURAN-1OL

Heat a mixture 6.0 g of the title compound of Example 7B, 60 mL of dioxane and 60 mL of 10% aqueous oxalic acid is heated at reflux for 8 hr. Cool the reaction mixture and pour the cooled reaction mixture into 300 mL of brine-$H_2O$-10% aqueous $K_2CO_3$ (10:10:1, v/v/v). Extract with EtOAc. Wash with combined extracts with brine. Dry over anhydrous $Na_2SO_4$, filter and evaporate to give a residue. Chromatograph the residue on silica gel eluting with EtOAc-$CH_2Cl_2$. Evaporate the product-containing fractions to give a solid. Wash the solid with diisopropyl ether and dry to leave 3.8 g of the title compound, mp 215°–217° C.

D.
1-(4-CHLOROPHENYL)-1-(2-HYDROXYMETHYL)PHENYL-2-(1H-1,2,4-TRIAZOL-1-YL)ETHANOL

Treat a stirred solution of 1.4 g of the title compound of Example 7 C in 200 mL 10% aqueous EtOH with 0.2 g portions of $NaBH_4$ at 1 hr. intervals for 4 hr (total 0.8 g). Evaporate the mixture. Partition the residue so formed with EtOAc-brine. Dry the EtoAc over anyhydrous $Na_2SO_4$, filter and evaporate to give a residue. Chromatograph the residue on silica gel eluting with EtOAc-$CH_2Cl_2$ to afford 0.21 g of the title compound, mp 130°–193° C.

Calc. for $C_{17}H_{16}ClN_3O_2$: C, 61.92; H, 4.89; N, 12.74. Found: C, 61.86; H, 4.63; N, 12.51.

E.
1-(4-CHLOROPHENYL)-1-(1H-1,2,4-TRIAZOL-1-YLMETHYL)-1,3-DIHYDROISOBENZOFURAN HYDROCHLORIDE

In exactly the same manner as Example 6C, treat 0.8 g of the alcohol of Example 7C to afford 0.4 g of the title compound, mp 188°–196° C.

EXAMPLE 9

SUBSTITUTED 1-PHENYL-1-(1H-IMIDAZOL-1-YLMETHYL)-1,3-DIHYDROISOBENZOFURANS

Follow the procedure of Example 4 except in the procedure of Example 4A substitute for 2-bromobenzyl(2-tetrahydropyranyl)ether, an equivalent quantity of a compound listed under column IIIa and for phenacyl chloride, an equivalent quantity of a compounds listed under column IVb:

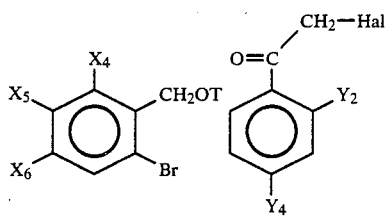

|     | $X_4$ | $X_5$ | $X_6$ | $Y_2$ | $Y_4$ |
| --- | --- | --- | --- | --- | --- |
| (a) | H | H | H | H | F |
| (b) | H | H | H | F | F |
| (c) | H | H | H | Cl | Cl |
| (d) | H | H | Cl | H | Cl |
| (e) | H | Cl | H | H | Cl |
| (f) | F | H | H | H | Cl |
| (g) | H | $CH_3O-$ | H | Cl | Cl |
| (h) | H | $\underline{n}$-$C_3H_7O-$ | H | F | F |
| (i) | H | H | H | H | $CF_3$ |
| (j) | H | H | $CF_3$ | H | Cl |
| (k) | H | Cl | H | H | $CH_3$ |
| (l) | H | Cl | H | H | $CH_3O$ |
| (m) | H | H | H | H | $CH_3S$ |
| (n) | H | H | H | H | 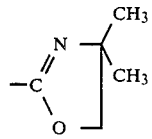 |

-continued

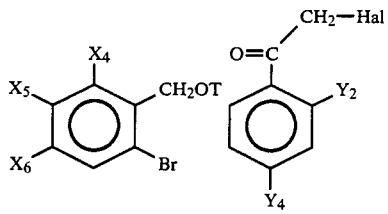

| | $X_4$ | $X_5$ | $X_6$ | $Y_2$ | $Y_4$ |
|---|---|---|---|---|---|
| (o) | H | H | H | H | −N(CH2CH2)2N−H (piperazinyl) |
| (p) | H | −N(Si(CH3)3)2 | H | H | H |
| (q) | H | H | −N(Si(CH3)3)2 | H | H |
| (r) | H | −C(=N)O−C(CH3)2 (oxazoline) | H | H | H |
| (s) | H | H | −C(=N)O−C(CH3)2 (oxazoline) | H | H |

Footnotes
(1) Formula IIIa is formula III wherein q = 1, and E = Br
(2) Formula IVb is formula IV wherein n = 0 and m = 1
(3) (a) use procedure described by A. Marver et al. J. Org. Chem. Vol. 40 (1975) pages 1427–1432.
(b) use procedure described by S. Djvric in Tetrahedron Letters, Vol. 22, p. 1787–1790 (1981).

to form after reaction with imidazolesodium and treatment with 6N HCl, respectively:

(a) 1-(4-fluorophenyl)-1-(1H-imidazol-1-ylmethyl)-1,3-dihydroisobenzofuran,
(b) 1-(2,4-difluorophenyl)-1-(1H-imidazol-1-ylmethyl)-1,3-dihydroisobenzofuran,
(c) 1-(2,4-dichlorophenyl)-1-(1H-imidazol-1-ylmethyl)-1,3-dihydroisobenzofuran,
(d) 1-(4-chlorophenyl)-1-(1H-imidazol-1-ylmethyl)-1,3-dihydro-6-chloroisobenzofuran,
(e) 1-(4-chlorophenyl)-1-(1H-imidazol-1-ylmethyl)-1,3-dihydro-5-chloroisobenzofuran
(f) 1-(4-chlorophenyl)-1-(1H-imidazol-1-ylmethyl)-1,3-dihydro-4-fluoroisobenzofuran,
(g) 1-(2,4-dichlorophenyl)-1-(1H-imidazol-1-ylmethyl)-1,3-dihydro-5-methoxyisobenzofuran,
(h) 1-(2,4-diuorophenyl)-1-(1H-imidazol-1-ylmethyl)-1,3-dihydro-5-n-propoxyisobenzofuran,
(i) 1-(4-trifluoromethylphenyl)-1-(1H-imidazol-1-ylmethyl)-1,3-dihydroisobenzofuran,
(j) 1-(4-chlorophenyl)-1-(1H-imidazol-1-ylmethyl)-1,3-dihydro-4-trifluoromethylisobenzofuran,
(k) 1-(4-methylphenyl)-1-(1H-imidazol-1-ylmethyl)-1,3-dihydro-5-chloroisobenzofuran,
(l) 1-(4-methoxyphenyl)-1-(1H-imidazol-1-ylmethyl)-1,3-dihydro-5-chloroisobenzofuran,
(m) 1-(4-methylthiophenyl)-1-(1H-imidazol-1-ylmethyl)-1,3-dihydroisobenzofuran,
(n) 1-(4-carboxyphenyl)-1-(1H-imidazol-1-ylmethyl)-1,3-dihydroisobenzofuran,
(o) 1-(4-piperdinyl)-1-(1H-imidazol-1-ylmethyl)-1,3-dihydroisobenzofuran,
(p) 1-phenyl-1-(1-H-imidazol-1-ylmethyl)-5-amino-1,3-dihydroisobenzofuran,
(q) 1-phenyl-1-(1H-imidazol-1-ylmethyl)-6-amino-1,3-dihydroisobenzofuran, (r) 1-phenyl-1-(1H-imidazol-1-ylmethyl)-5-carboxyl-1,3-dihydroisobenzofuran, and (s) 1-phenyl-1-(1H-imidazol-1-ylmethyl)-6-carboxy-1,3-dihydroisobenzofuran.

EXAMPLE 10

SUBSTITUTED 1-PHENYL-1-(1H-1,2,4-TRIAZOL-1-YLMETHYL)-1,3-DIHYDROISOBENZOFURANS

Follow the procedure of Example 9 except that substitute for imadazolesodium, an equivalent quantity of triazolesodium to form the title compounds of this Example corresponding to compounds (a) to (s) of Example 9 of except that 1-(1H-1,2,4-triazol-1-ylmethyl) is substituted for 1-(1H-imidazol-1-ylmethyl).

EXAMPLE 11

ESTER, KETONE TRIFLUOROMETHYL AND AMIDE DERIVATIVES OF 1-(4-CARBOXYPHENYL)-1-(1H-IMIDAZOL-1-YLMETHYL)-1,3-DIHYDROISOBENZOFURAN and 1-(4-CARBOXYPHENYL)-1-(1H-1,2,4-TRIAZOL-1-YLMETHYL)-1,3-DIHYDROISOBENZOFURAN Compounds (n) of Examples 9 and 10 are converted into the esters, ketone trifluoromethyl and amides listed in the table below by utilizing the appropriate standard chemical reagents

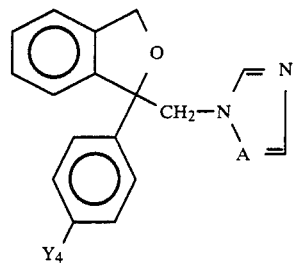

| | $Y_4$ | A | | $Y_4$ | A |
|---|---|---|---|---|---|
| (a) | $-\overset{O}{\underset{\|\|}{C}}-OC_2H_5$ | CH | (i) | $-\overset{O}{\underset{\|\|}{C}}-N\diagup\diagdown$ | CH |
| (b) | $-\overset{O}{\underset{\|\|}{C}}-OC_2H_5$ | N | (j) | $-\overset{O}{\underset{\|\|}{C}}-N\diagup\diagdown$ | N |
| (c) | $-\overset{O}{\underset{\|\|}{C}}-OCH_3$ | CH | (k) | $-\overset{O}{\underset{\|\|}{C}}-N\diagup\diagdown$ | CH |
| (d) | $-\overset{O}{\underset{\|\|}{C}}-OCH_3$ | N | (l) | $-\overset{O}{\underset{\|\|}{C}}-N\diagup\diagdown$ | N |
| (e) | $-\overset{O}{\underset{\|\|}{C}}-CH_3$ | CH | (m) | $-\overset{O}{\underset{\|\|}{C}}-N\diagup\diagdown$ | CH |
| (f) | $-\overset{O}{\underset{\|\|}{C}}-CH_3$ | N | (n) | $-\overset{O}{\underset{\|\|}{C}}-N\diagup\diagdown$ | N |
| (g) | $-\overset{O}{\underset{\|\|}{C}}-N(CH_3)_2$ | CH | (o) | $-CF_3$ | CH |
| (h) | $-\overset{O}{\underset{\|\|}{C}}-N(CH_3)$ | N | (p) | $-CF_3$ | N |

EXAMPLE 12

ESTER, KETONE, TRIFLUOROMETHYL AND AMIDE DERIVATIVES OF 1-PHENYL-1-(1H-IMIDAZOL-1-YLMETHYL)-5-CARBOXY-1,3-DIHYDROISOBENZOFURAN, 1-PHENYL-1-(1H-1,2,4-TRIAZOL-1-YLMETHYL)-5-CARBOXY-1,3-DIHYDROISOBENZOFURAN, 1-PHENYL-1-(1H-IMIDAZOL-1-YLMETHYL)-6-CARBOXY-1,3-DIHYDROISOBENZOFURAN and 1-PHENYL-1(1H-1,2,4-TRIAZOL-1-YLMETHYL)-5-CARBOXY-1,3-DIHYDROISOBENZOFURAN Compounds (r) and (s) of Examples 9 and 10 are converted into the esters, ketone, trifluoromethyl and amides, listed in table below by utilizing the appropriate standard chemical reagents

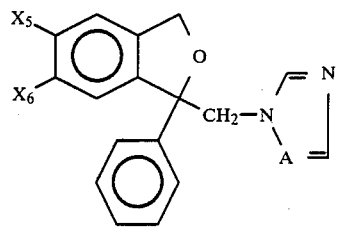

| | $X_5$ | $X_6$ | A |
|---|---|---|---|
| (1) | H | $-\overset{O}{\underset{\|\|}{C}}-OC_2H_5$ | CH |
| (2) | H | $-\overset{O}{\underset{\|\|}{C}}-OC_2H_5$ | N |
| (3) | $-\overset{O}{\underset{\|\|}{C}}-OC_2H_5$ | H | CH |
| (4) | $-\overset{O}{\underset{\|\|}{C}}-OC_2H_5$ | H | N |

-continued

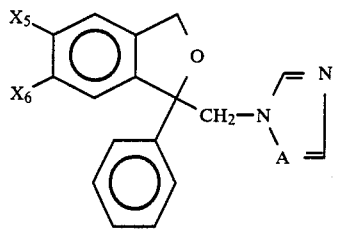

| | $X_5$ | $X_6$ | A |
|---|---|---|---|
| (5) | H | -C(O)-CH₃ | CH |
| (6) | H | -C(O)-CH₃ | N |
| (7) | -C(O)-CH₃ | H | CH |
| (8) | -C(O)-CH₃ | H | N |
| (9) | H | -C(O)-N(CH₃)₂ | CH |
| (10) | H | -C(O)-N(CH₃)₂ | N |
| (11) | -C(O)-N(CH₃)₂ | H | CH |
| (12) | -C(O)-N(CH₃)₂ | H | N |
| (13) | H | -C(O)-piperidinyl | CH |
| (14) | H | -C(O)-piperidinyl | N |
| (15) | -C(O)-piperidinyl | H | CH |
| (16) | -C(O)-piperidinyl | H | N |
| (17) | H | -C(O)-morpholinyl | CH |
| (18) | H | -C(O)-morpholinyl | N |

-continued

| | $X_5$ | $X_6$ | A |
|---|---|---|---|
| (19) | -C(O)-morpholinyl | H | CH |
| (20) | -C(O)-morpholinyl | H | N |
| (21) | H | -C(O)-pyrrolidinyl | CH |
| (22) | H | -C(O)-pyrrolidinyl | N |
| (23) | -C(O)-pyrrolidinyl | H | CH |
| (24) | -C(O)-pyrrolidinyl | H | N |
| (25) | H | -CF₃ | CH |
| (26) | H | -CF₃ | N |
| (27) | -CF₃ | H | CH |
| (28) | -CF₃ | H | N |

EXAMPLE 13

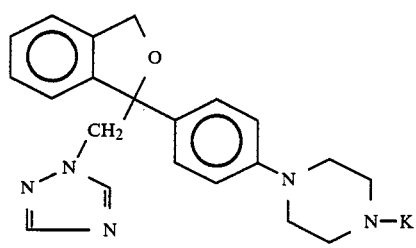

XX

The compound represented by formula XX listed above wherein K is H and A is CH or N, prepared in accordance with the produces of Examples 9(o) and 10(o) is converted into compound having formula wherein

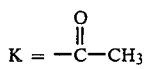

by utilizing standard acetylation reagents. The compound represented by formula XX wherein A is CH or N and K is

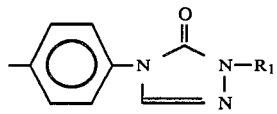

wherein R' is lower alkyl such as $CH_3-$, $C_2H_5-$, $i-C_3H_5$, $n-C_4H_5-$ or $-CH(CH_3)C_2H_5$ is prepared by use of the procedures of Heeres et al. [J. Med. Chem., Vol. 27 (1984) pages 894–900 except that an equivalent amount of compounds of Examples 9(o) and 10(o), are substituted respectively for cis-1-[4-[[2-(2,4-dichlorophenyl)-2(1H-1,2,4-triazol-1-ylmethyl)-1,3-dioxolan-4-yl]methoxy]phenyl]-4-(4-nitrophenyl)piperazine compound 66 in the Heeres reference.

EXAMPLE 14

DERIVATIVES OF 1-PHENYL-1-(1H-IMIDAZOL-1-YLMETHYL)-5-AMINO-1,3-DIHYDROISOBENZOFURAN, 1-PHENYL-1-(1H-1,2,4-TRIAZOL-1-YLMETHYL)-5-AMINO-1,3-DIHYDROISOBENZOFURAN, 1-PHENYL-1-(1H-IMIDAZOL-1-YLMETHYL)-6-AMINO-1,3-DIHYDROISOBENZOFURAN and 1-PHENYL-1-(1H-1,2,4-TRIAZOL-1-YLMETHYL)-6-AMINO-1,3-DIHYDROISOBENZOFURAN Compounds (p) and (q) of Examples 9 and 10 are converted into the derivatives listed below by utilizing standard chemical reagents

| | $X_5$ | $X_6$ | A | | $X_5$ | $X_6$ | A |
|---|---|---|---|---|---|---|---|
| (a) | H | $-N(CH_3)_2$ | CH | (k) | | $-N$(piperidinyl) | H | CH |
| (b) | H | $-N(CH_3)_2$ | N | (l) | | $-N$(piperidinyl) | H | N |
| (c) | $-N(CH_3)_2$ | H | CH | (m) | H | $-N$(morpholinyl)$O^1$ | CH |
| (d) | $-N(CH_3)_2$ | H | N | (n) | H | $-N$(morpholinyl)$O^1$ | N |
| (e) | $-H$ | $-N(C_2H_5)C(O)CH_3$ | CH | (o) | | $-N$(morpholinyl)$O^1$ | H | CH |
| (f) | H | $-N(C_2H_5)C(O)CH_3$ | N | (p) | | $-N$(morpholinyl)$O^1$ | H | N |
| (g) | $-N(C_2H_5)C(O)CH_3$ | | H | (q) | H | $-N$(pyrrolidinyl) | | CH |

-continued

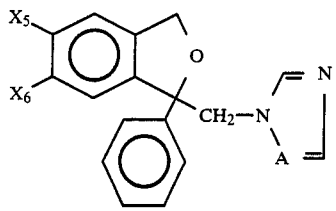

| | X₅ | X₆ | A | | X₅ | X₆ | A |
|---|---|---|---|---|---|---|---|
| (h) | | −N(C₂H₅)−C(=O)−CH₃ | H | N | (r) | H | −N(pyrrolidinyl) | N |
| (i) | H | −N(piperidinyl) | | CH | (s) | | −N(pyrrolidinyl) | H | CH |
| (j) | H | −N(piperidinyl) | | N | (t) | | −N(pyrrolidinyl) | H | N |

[1] Use procedure of USP 3,876,640 at Cols 2, 6 (step A), 8 (step D) and 10 (step E).

EXAMPLE 15

SUBSTITUTED 1-BENZYL-1-(1H-IMADAZOL-1-YLMETHYL)1,3-DIHYDROISOBENZOFURANS

Follow the procedure of Example 4, except in procedure of Example 4A, substitute for 2-bromobenzyl(2-tetrahydropyranyl)ether, an equivalent quantity of a compound listed under column IIIa and for phenacyl chloride, an equivalent quantity of a compound listed under column IVc (formula IV wherein n=m=1)

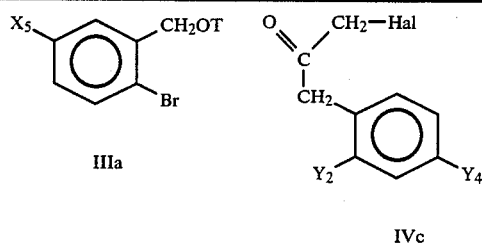

| | X₅ | Y₂ | Y₄ |
|---|---|---|---|
| (a) | H | H | Cl |
| (b) | H | Cl | Cl |
| (c) | H | H | F |
| (d) | Cl | H | CH₃O |
| (e) | H | H | CF₃ |
| (f) | H | H | H | to form after reaction with imadazolesodium and treatment with 6N HCl, respectively:

(a) 1-(4-chlorobenzyl)-1-(1H-imidazol-1-ylmethyl)1,3-dihydroibenzofuran,
(b) 1-(2,4-dichlorobenzyl)-1-(1H-imidazol-1-ylmethyl)-1,3-dihydroisobenzofuran,
(c) 1-(4-fluorobenzyl)-1-(1H-imidazol-1-ylmethyl)-1,3-dihydroisobenzofuran,
(d) 1-(4-methoxybenzyl)-1-(1H-imidazol-1-ylmethyl)-1,3-dihydro-5-chloroisobenzofuran,
(e) 1-(4-trifluoromethylbenzyl)-1-(1H-imidazol-1-ylmethyl)-1,3-dihydroisobenzofuran, and
(f) 1-benzyl-1-(1H-imidazol-1-ylmethyl)-1,3-dihydroisobenzofuran.

EXAMPLE 16

SUBSTITUTED-1-BENZYL-1-(1H-1,2,4-TRIAZOL-1-YLMETHYL)1,3-DIHYDROISOBENZOFURANS

Follow the procedure of Example 15, except substitue for imidazolesodium, an equivalent quantity of triazolesodium to form the title compounds of this Example corresponding to compounds (a) to (f) of Example 15 except that 1-(1H-1,2,4-triazol-1-ylmethyl) is substituted for 1-(1H-imidazol-1-ylmethyl).

EXAMPLE 17

SUBSTITUTED 1-PHENYL-1-[2-(1H-IMIDAZOL-1-YLMETHYL) OR -[2-(1H-1,2,4-TRIZAOL-1-YLETHYL]-1,3-DIHYROISOBENZOFURANS

Follow the procedure of Example 4A except substituted for 2-bromobenzyl(2-tetrahydropyranyl)ether, an equivalent quantity of a compound listed under column IIIa and for phenacyl chloride, an equivalent quantity of a compound listed under column VIIIa.

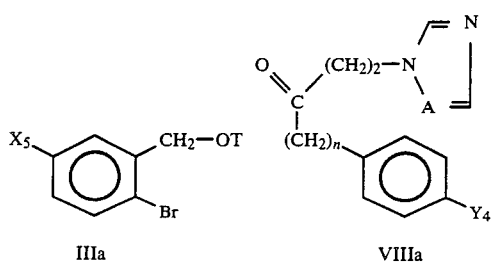

| | $X_5$ | $Y_4$ | n | A |
|---|---|---|---|---|
| (a) | H | Cl | 0 | CH |
| (b) | H | Cl | 1 | CH |
| (c) | H | Cl | 0 | N |
| (d) | H | Cl | 1 | N |
| (e) | H | F | 0 | CH |
| (f) | H | F | 1 | CH |
| (g) | H | F | 0 | N |
| (h) | H | F | 1 | N |
| (i) | Cl | $CH_3$ | 0 | CH |
| (j) | Cl | $CH_3$ | 1 | CH |
| (k) | Cl | $CH_3$ | 0 | N |
| (l) | Cl | $CH_3$ | 1 | N |
| (m) | Cl | $CH_3O$ | 0 | CH |
| (n) | Cl | $CH_3O$ | 1 | CH |
| (o) | Cl | $CH_3O$ | 0 | N |
| (p) | Cl | $CH_3O$ | 1 | N | to form after treatment with imidazolesodium and 6N HCl respectively:

(a) 1-(4-chlorophenyl)-1-[2-(1H-imidazol-1-yl)ethyl]1,3-dihydroisobenzofuran, (b) 1-(4-chlorobenzyl)-1-[2-(1H-imidazol-1yl)ethyl]1,3-dihydroisobenzofuran, (c) 1-(4-chlorophenyl)-1-[2-(1H-1,2,4-triazol-1-yl)ethyl]-1,3-dihydroisobenzofuran, (d) 1(4-chlorobenzyl)-1-[2-(1H-1,2,4-triazol-1-yl)ethyl]-1,3-dihydroisobenzofuran, (e) 1-(4-fluorophenyl)-1[2-(1H-imidazol-1-yl)ethyl]-1,3-dihydroisobenzofuran, (f) 1-(4-fluorobenzyl)-1-[2-(1H-imidazol-1-yl)ethyl)-1,3-dihydroisobenzofuran, (g) 1-(4-fluorophenyl)-1-[2-(1H-1,2,4-triazol-1-yl)ethyl]-1,3-dihydroisobenzofurnan, (h) 1-(4-fluorobenzyl)-1-[2-(1H-1,2,4-triazol-1-yl)ethyl]-1,3-dihydroisobenzofuran, (i) 1-(4-methylphenyl)-1-[2-(1H-imidazol-1-yl)ethyl]-1,3-dihydro-5-chloroisobenzofuran, (j) 1-(4-methylbenzyl)-1-[2-(1H-imidazol-1-yl)ethyl]-1,3-dihydro-5-chloroisobenzofuran, (k) 1-(4-methylphenyl)-1-[2-(1H-1,2,4-triazol-1-yl)ethyl]-1,3-dihydro-5-chloroisobenzofuran.

(l) 1-(4-methylbenzyl)-1-[2-(1H-1,2,4-triazol-1-yl)ethyl]-1,3-dihydro-5-chloroisobenzofuran, (m) 1-(4-methoxyphenyl)-1-[2-(1H-imidazol-1-yl)ethyl]-1,3-dihydro-5-chloroisobenzofuran, (n) 1-(4-methoxybenzyl)-1-[2-(1H-imidazol-1-yl)ethyl]-1,3-dihydro-5-chloroisobenzofuran, (o) 1-(4-methoxyphenyl)-1-[2-(1H-1,2,4-triazol-1-yl)ethyl]-1,3-dihydro-5-chloroisobenzofuran, and (p) 1-(4-methoxybenzyl)-1-[2-(1H-1,2,4-triazol-1-yl)ethyl]-1,3-dihydro-5-chloroisobenzofuran.

EXAMPLE 18

1-(4-CHLOROPHENYL)-1-(1H-IMIDAZOL-1-YLMETHYL)-3,4-DIHYDROISOCHROMAN HYDROCHLORIDE

The title compound, a white solid having mp 154°–158° C. is prepared in accordance with the procedures of Example 4 except that in procedure 4A an equivalent quantity of 2-(2-bromophenyl)ethanol is substituted for 2-bromobenzyl alcohol.

EXAMPLE 19

SUBSTITUTED 1-PHENYL- OR 1-BENZYL-1-(1H-IMIDAZOL-1-YLMETHYL)-3,4-DIHYDROISOCHROMANS

Follow the procedure of Example 4 except in procedure 6A substitute for 2-bromobenzyl(2-tetrahyropyranyl)ether, an equivalent quantity of the compound listed under column IIIb and for phenacyl chloride, an equivalent quantity of a compound listed under column IVa

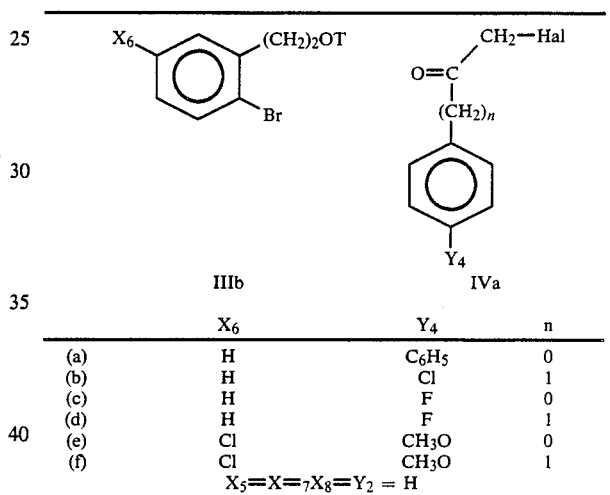

| | $X_6$ | $Y_4$ | n |
|---|---|---|---|
| (a) | H | $C_6H_5$ | 0 |
| (b) | H | Cl | 1 |
| (c) | H | F | 0 |
| (d) | H | F | 1 |
| (e) | Cl | $CH_3O$ | 0 |
| (f) | Cl | $CH_3O$ | 1 |

$X_5=X_7=X_8=Y_2=H$

[1] Formula III wherein q = 2 and E is Br
[2] Formula IV wherein m = 1.

to obtain after treatment with imidazolesodium and 6N HCl, respectively:

(a) 1-[(4,1'-biphenyl)yl]-1-(1H-imidazol-1-ylmethyl)-3,4-dihydroisochroman, (b) 1-[(4-chlorobenzyl)-1-(1H-imidazol-1-ylmethyl)-3,4-dihydroisochroman, (c) 1-(4-fluorophenyl)-1-(1H-imidazol-1-ylmethyl)-3,4-dihydroisochroman, (d) 1-(4-fluorobenzyl)-1-(1H-imidazol-1-ylmethyl)-3,4-dihydroisochroman, (e) 1-(4-methoxyphenyl)-1-(1H-imidazol-1-ylmethyl)-3,4-dihydro-7-chloroisochroman, and (f) 1-(4-methoxyphenyl)-1-(1H-imidazol-1-ylmethyl)-3,4-dihydro-7-chloroisochroman.

EXAMPLE 20

SUBSTITUTED 1-PHENYL- OR 1-BENZYL-1-(1H-1,2,4-TRIAZOL-1-YLMETHYL)-3,4-DIHYDROISCHROMANS

Follow the procedure of Example 19 except substitute for imidazolesodium an equivalent quantity of triazolesodium to form the title compound of this Example corresponding to compounds (a) to (f) of Example 19 except that 1-(1H-1,2,4-triazol-1-ylmethyl) is substituted for 1-(1H-imidazol-1-ylmethyl).

EXAMPLE 21

SUBSTITUTED 1-PHENYL- OR 1-BENZYL-1-(1H-IMIDAZOL-1-YLMETHYL)-1,3-DIHYDROBENZO[c]THIOPHENES

Follow the procedure of Example 4 except substitute for 2-bromobenzyl(2-tetrahyropyranyl)ether, an equivalent quantity of a compound listed under column Xa and for phenacyl chloride, an equivalent quantity of a compound listed under column IVc

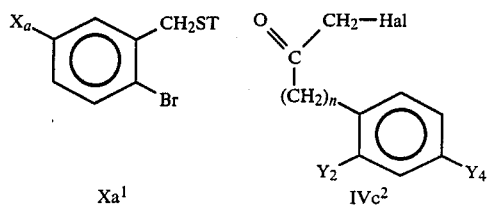

| | $Y_5$ | $Y_2$ | $Y_4$ | n |
|---|---|---|---|---|
| (a) | H | H | Cl | 0 |
| (b) | H | H | Cl | 1 |
| (c) | H | H | F | 0 |
| (d) | H | H | F | 1 |
| (e) | H | H | H | 0 |
| (f) | H | H | H | 1 |
| (g) | Cl | Cl | Cl | 0 |
| (h) | Cl | Cl | Cl | 1 |
| (i) | Cl | H | CH$_3$O— | 0 |
| (j) | Cl | H | CH$_3$O— | 1 |
| (k) | Cl | H | H | 0 |
| (l) | Cl | H | H | 1 |

[1]Formula X wherein E is Br, q = 1.
[2]Formula IV wherein m = 1.

to form after treatment with imidazolesodium and 6N HCl respectively:
(a) 1-(4-chlorophenyl)-1-(1H-imidazol-1-ylmthl)-1,3-dihydroibenzo[c]thiophene,
(b) 1-(4-chlorobenzyl)-1-(1H-imidazol-1-ylmethyl)-1,3-dihydrobenzo[c]thiophene,
(c) 1-(4-fluorophenyl)-1-(1H-imidazol-1-ylmethyl)-1,3-dihydrobenzo[c]thiophene,
(d) 1-(4-dluorobenzyl)-1-(1H-imidazol-1-ylmethyl)-1,3-dihydrobenzo[c]thiophene,
(e) 1-phenyl-1-(1H-imidazol-1-ylmethyl)-1,3-dihydrobenzo[c]thiophene,
(f) 1-benzyl-1-(1H-imidazol-1-ylmethyl)-1,3-dihydrobenzo[c]thiophene,
(g) 1-(2,4-dichlorophenyl)-1-(1H-imidazol-1-ylmethyl)-1,3-dihydro-5-chlorobenzo[c]thiophene,
(h) 1-(2,4-dichlorobenzyl)-1-(1H-imidazol-1-ylmethyl)-1,3-dihydro-5-chlorobenzo[c]thiophene,
(i) 1-(4-methoxyphenyl)-1-(1H-imidazol-1-ylmetyl)-1,3-dihydro-5-chlorobenzo[c]thiophene,
(j) 1-(4-methoxybenzyl)-1-(1H-imidazol-1-ylmethyl)-1,3-dihydro-5-chlorobenzo[c]thiophene,
(k) 1-phenyl-1-(1H-imidazol-1-ylmethyl)-1,3-dihydro-5-chlorobenzo[c]thiophene, and
(l) 1-benzyl-1-(1H-imidazol-1-ylmethyl)-1,3-dihydro-5-chlorobenzo[c]thiophene.

EXAMPLE 22

SUBSTITUTED 1-PHENYL- AND 1-BENZYL-(1H-1,2,4-TRIAZOL-1-YLMETHYL)-1,3-DIHYDROBENZO[c]THIOPHENES

Follow the procedure of Example 21 except substitute for imidazolesodium, an equivalent quantity of triazolesodium to form the title compounds of this Example corresponding to compounds (a) to (l) of Example 21 except that 1-(1H-1,2,4-triazol-1-ylmethyl) is substituted for 1-(1H-imidazol-1-ylmethyl).

EXAMPLE 23

SUBSTITUTED 1-PHENYL AND 1-BENZYL-1-(1H-IMIDAZOL-1-YLMETHYL-3,4-DIHYDROISOTHIOCHROMANS

Follow the procedure of Example 4 except in procedure 4A substitute for 2-bromobenzyl(2-tetrahydropyranyl)ether an equivalent amount of a compound listed in column Xb and for phenacyl chloride, an equivalent quantity of a compound listed under column IVa.

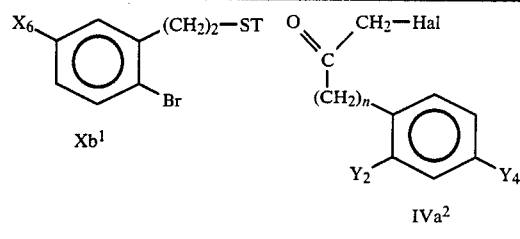

| | $X_6$ | $Y_2$ | $Y_4$ | n |
|---|---|---|---|---|
| (a) | H | H | H | 0 |
| (b) | H | H | H | 1 |
| (c) | H | H | Cl | 0 |
| (d) | H | H | Cl | 1 |
| (e) | Cl | H | H | 0 |
| (f) | Cl | H | H | 1 |
| (g) | F | H | H | 0 |
| (h) | F | H | H | 1 |
| (i) | H | H | F | 0 |
| (j) | H | H | F | 1 |
| (k) | CH$_3$O | H | H | 0 |
| (l) | CH$_3$O | H | H | 1 |
| (m) | H | H | CF$_3$ | 0 |
| (n) | H | H | CF$_3$ | 1 |
| (o) | H | F | F | 0 |
| (p) | H | F | F | 1 |
| (q) | H | Cl | Cl | 0 |
| (r) | H | Cl | Cl | 1 |

[1]Formula X wherein E is Br, and
[2]Formula IV wherein m = 1.

to form after with imidazolesodium and 6N HCl, respectively:
(a) 1-phenyl-1-(1H-imidazol-1-ylmethyl)-3,4-dihydroisoithiochroman,
(b) 1-benzyl-1-(1H-imidazol-1-ylmethyl)-3,4-dihydroisoithiochroman,
(c) 1-(4-chlorophenyl)-1-(1H-imidazol-1-ylmethyl)-3,4-dihydroisothiochroman,
(d) 1-(4-chlorobenzyl)-1-(1H-imidazol-1-ylmethyl)-3,4-dihydroisothiochroman,
(e) 1-phenyl-1-(1H-imidazol-1-ylmethyl)-3,4-dihydro-6-chloroisothiochroman,
(f) 1-benzyl-1-(1H-imidazol-1-ylmethyl)-3,4-dihydro-6-chloroisothiochroman, (g) 1-phenyl-1-(1H-imidazol-1-ylmethyl)-3,4-dihydro-6-fluoroisothiochroman, (h) 1-benzyl-1-(1H-imidazol-1-ylmethyl)-3,4-dihydro-6-fluoroisothiochroman, (i) 1-(4-fluorophenyl)-1)-(1H-imidazol-1-ylmethyl)-3,4-dihydroisothiochroman.

(j) 1-(4-fluorobenzyl)-1-(1H-imidazol-1-ylmethyl)-3,4-dihydroisothiochroman, (k) 1-phenyl-1-(1H-imidazol-1-ylmethyl)-3,4-dihydro-6-methoxyisothiochroman, (l) 1-benzyl-1-(1H-imidazol-1-ylmethyl)-3,4-dihydro-6-methoxyisothiochroman, (m) 1-(4-trifluoromethylphenyl)-1-(1H-imidazol-1-ylmethyl)-3,4-dihydroisothiochroman, (n) 1-(4-trifluoromethylbenzyl)-1-(1H-imidazol-1-ylmethyl)-3,4-dihydroisothiochroman, (o) 1-(2,4-difluorophenyl)-1-(1H-imidazol-1-ylmethyl)-3,4-dihydroisothiochroman, (p) 1-(2,4-difluorobenzyl)-1-(1H-imidazol-1-ylmethyl)-3,4-dihydroisothiochroman, (q) 1-(2,4-dichlorophenyl)-1-(1H-imidazol-1-ylmethyl)-3,4-dihydroisothiochroman, and (r) 1-(2,4-dichlorobenzyl)-1-(1H-imidazol--ylmethyl)-3,4-dihyroisothiochroman.

EXAMPLE 24

SUBSTITUTED 1-PHENYL- AND 1-BENZYL-1-(1H-1,2,4-TRIAZOL--YLMETHYL)-3,4-DIHYDROISOTHIOCHROMAN

Follow the procedure of Example 23 except substitue for imidazolesodium an equivalent quantity of traizolesodium to form the title compounds of this Example corresponding to compound (a) to (r) of Example 23 except that 1-(1H-1,2,4-triazol-1-ylmethyl) is substituted for 1-(1H-imidazol-1-ylmethyl).

EXAMPLE 25

The following are typical pharmaceutical formulations containing as the active ingredient (designated "Drug") a compound of this invention, such as 1-(4-chlorophenyl)-1-(1H-imidazol-1-ylmethyl)-1,3-dihydroisobenzofuran or 1-(4-chlorophenyl)-1-(1H-imidazol-1-ylmethyl)-1,3-dihydro-4,6-dichloroisobenzofuran or 1-(4-chlorophenyl)-1-(1H-imidazol-1-ylmethyl)-3,4-dihydroisochroman. It will be appreciated, however, that each of these compounds may be be replaced by equally effective quantities of other compounds represented by formula I.

| FORMULATION 1 | |
|---|---|
| Tablet 125.00 mg. tab. | |
| Drug | 125.00 mg. |
| Polyethylene glycol 6000 | 100.00 mg. |
| Sodium lauryl sulfate | 6.25 mg. |
| Corn starch | 30.00 mg. |
| Lactose, anhydrous | 87.25 mg. |
| Magnesium stearate | 1.50 mg. |

Procedure

Heat the polyethylene glycol 6000 to 70°–80° C. Mix the drug, sodium lauryl sulfate, corn starch, and lactose into the liquid and allow the mixture to cool. Pass the solidified mixture through a mill. Blend granules with magnesium stearate and compress into tablets.

| FORMULATION 2 | |
|---|---|
| Capsule 250 mg. tab. | |
| Drug | 250.00 mg. |
| Lactose, anhydrous | 100.00 mg. |
| Corn Starch | 50.00 mg. |
| Microcrystalline cellulose | 95.00 mg. |
| Magnesium stearate | 5.00 mg. |

Procedure

Mix the first four ingredients in a suitable mixer for 10–15 minutes. Add the magnesium stearate and mix for 1–3 minutes. Fill the mixture into suitable two-piece hard gelatin capsules using an encapsulating machine.

We claim:

1. A compound represented by the formula I:

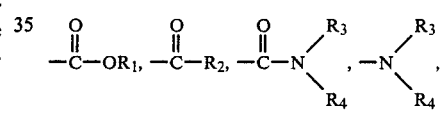

in racemic or optically active form or a pharmaceutically acceptable acid salt thereof, wherein A is CH or N;

X is independently at least one of hydrogen, halogen, perhaloloweralkyl, lower alkoxy, lower alkylthio,

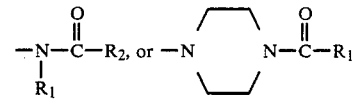

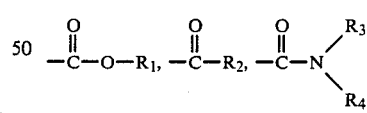

Y is independently at least one of hydrogen, halogen, lower alkyl, perhaloloweralkyl, lower alkoxy, lower alkylthio,

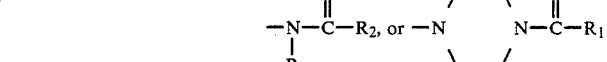

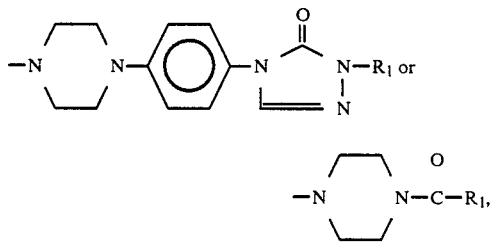

or X-substituted phenyl;

$R_1$ and $R_2$ are independently hydrogen or lower alkyl;

$R_3$ and $R_4$ are independently hydrogen, lower alkyl or when taken together with the adjacent nitrogen atom, a morpholino group, a piperazino group, a piperidino group or a pyrrolidino group;
Z is oxygen or sulfur;
m is 1 or 2;
n is 0, 1 or 2;
o and p are independently 1 to 4; and
q is 1 or 2.

2. A compound of claim 1 wherein Z is oxygen.

3. A compound of claim 1 wherein A is CH.

4. A compound of claim 1 wherein n is 0 and wherein Y is halogen.

5. The compound of claim 4 wherein Y is chlorine.

6. A compound of claim 1 wherein Y is a halogen-substituted phenyl.

7. The compound of claim 6 wherein Y is 4-chlorophenyl.

8. A compound of claim 1 wherein q and m each are 1.

9. A compound according to claim 1 which is 1-(4-chlorophenyl)-1-(1H-imidazol-1-ylmethyl)-1,3-dihydroisobenzofuran.

10. A compound according to claim 1 which is 1-(4-chlorophenyl)-1(1H-1,2,4-triazol-1-ylmethyl)-1,3-dihydroisobenzofuran.

11. A compound according to claim 1 which is 1-(2,4-dichlorophenyl)-1-(1H-imidazol-1-ylmethyl)-1,3-dihydro-4,6-dichloroisobenzofuran.

12. A compound according to claim 1 which is 1-(4-chlorophenyl-1-(1H-imidazol-1-ylmethyl)-3,4-dihydroisochroman.

13. A compound of claim 1 wherein A is N.

14. An antifungally effective phrarmaceutical composition comprising an antifungally effective amount of a compound of claim 1 in admixture with a pharmaceutically acceptable carrier or diluent therefor.

15. The composition according to claim 14 adapted for topical administration.

16. A method of treating susceptible fungal infections which comprises administering to a host in need of such treatment a compound of claim 1 or a pharmaceutical composition thereof in an amount sufficient to treat such infections.

17. The method according to claim 16 wherein the route of administration is topical.

18. A compound according to claim 1 which is 1-(2,4-dichlorophenyl)-1-(1H-imidazol-1-ylmethyl)-1,3-dihydroisobenzofuran.

* * * * *